United States Patent [19]

Greig

[11] 4,132,804

[45] Jan. 2, 1979

[54] PROCESS OF TREATING ASTHMA

[75] Inventor: Margaret E. Greig, Kalamazoo, Mich.

[73] Assignee: The Upjohn Company, Kalamazoo, Mich.

[21] Appl. No.: 792,090

[22] Filed: Apr. 28, 1977

Related U.S. Application Data

[63] Continuation of Ser. No. 665,639, Mar. 10, 1976, abandoned, which is a continuation of Ser. No. 573,051, Apr. 30, 1975, abandoned, which is a continuation of Ser. No. 479,211, Jun. 14, 1974, abandoned, which is a continuation-in-part of Ser. No. 384,818, Aug. 2, 1973, abandoned, which is a continuation of Ser. No. 258,352, May 31, 1972, abandoned.

[51] Int. Cl.$^2$ .................. A61K 31/19; A61K 31/215
[52] U.S. Cl. .................................. 424/317; 424/305
[58] Field of Search ........................... 424/317, 305

[56] References Cited

PUBLICATIONS

Chem. Abst., vol. 74-3436K & 3438N (1971).

Physician's Desk Reference 25th Ed. pp. 990-991 (1971).

*Primary Examiner*—Stanley J. Friedman
*Attorney, Agent, or Firm*—John J. Killinger; Roman Saliwanchik

[57] ABSTRACT

A process for the therapeutic and prophylactic treatment of allergy by the systemic administration of a compound of the formula:

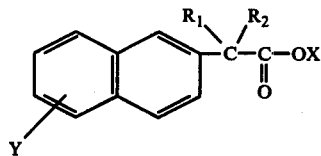

Formula I wherein Y is lower alkyl of 1 to 8 carbon atoms, cyclopropyl, ethinyl, $-CF_3$, $-F$, $-Cl$, $-OCH_3$, $-OCHF_2$, $-OCH_2OCH_3$, $-SCH_3$, $-SCHF_2$, $-SCH_2OCH_3$, acetyl; $R_1$ and $R_2$ are H, $CH_3$, $CHF_2$, or taken together are $=CH_2$ or $=CF_2$; and X is hydrogen, lower alkyl of 1 to 8 carbon atoms or a pharmacologically acceptable cation in association with a pharmaceutical carrier.

3 Claims, No Drawings

PROCESS OF TREATING ASTHMA

CROSS REFERENCE TO RELATED APPLICATIONS

This application is a continuation of application Ser. No. 665,639, filed Mar. 10, 1976, now abandoned which in turn is a continuation of application Ser. No. 573,051, filed Apr. 30, 1975, now abandoned which in turn is a continuation of application Ser. No. 479,211, filed June 14, 1974, now abandoned, which in turn is a continuation-in-part of application Ser. No. 384,818, filed Aug. 2, 1973, now abandoned, which in turn is a continuation of application Ser. No. 258,352, filed May 31, 1972, now abandoned.

BRIEF DESCRIPTION OF THE INVENTION

This invention relates to a novel method for therapeutic and prophylactic treatment of allergic conditions by the systemic administration of a compound of the formula I to a human or animal subject.

DETAILED DESCRIPTION OF THE INVENTION

The compound of the formula I are old compounds known in the art. The compounds are depicted in the protonated or acid form, however, for the purposes of the instant invention the proton can be replaced by any pharmacologically acceptable cation.

The compositions of the present invention are presented for administration to humans and animals in unit dosage forms, such as tablets, capsules, pills, powders, granules, sterile parenteral solutions or suspensions, and oral solutions or suspensions, and oil-in-water and water-in-oil emulsions containing suitable quantities of the compound of formula I. Another route of administration is by inhalation into the lung by means of an aerosol or powder for insufflation.

For oral administration either solid or fluid unit dosage forms can be prepared. For preparing solid compositions such as tablets, the compound of formula I is mixed with conventional ingredients such as talc, magnesium stearate, dicalcium phosphate, magnesium aluminum silicate, calcium sulfate, starch, lactose, acacia, methylcellulose, and functionally similar materials as pharmaceutical diluents or carriers. Capsules are prepared by mixing the compound with an inert pharmaceutical diluent and filling the mixture into a hard gelatin capsule of appropriate size. Soft gelatin capsules are prepared by machine encapsulation of a slurry of the compound with an acceptable vegetable oil, light liquid petrolatum or other inert oil.

Fluid unit dosage forms for oral administration such as syrups, elixirs, and suspensions can be prepared. The water-soluble forms can be dissolved in an aqueous vehicle together with sugar, aromatic flavoring agents and preservatives to form a syrup. An elixir is prepared by using a hydro-alcoholic (ethanol) vehicle with suitable sweeteners such as sugar and saccharin, together with an aromatic flavoring agent.

Suspensions can be prepared with a syrup vehicle with the aid of a suspending agent such as acacia, tragacanth, methylcellulose and the like.

For parenteral administration, fluid unit dosage forms are prepared utilizing the compound and a sterile vehicle, water being preferred. The compound, depending on the vehicle and concentration used, can be either suspended or dissolved in the vehicle. In preparing solutions the compound can be dissolved in water for injection and filter sterilized before filling into a suitable vial or ampul and sealing. Advantageously, adjuvants such as a local anesthetic, preservative and buffering agents can be dissolved in the vehicle. To enhance the stability, the composition can be frozen after filling into the vial and the water removed under vacuum. The dry lyophilized powder is then sealed in the vial and an accompanying vial of water for injection is supplied to reconstitute the liquid prior to use. Parenteral suspensions are prepared in substantially the same manner except that the compound is suspended in the vehicle instead of being dissolved and sterilization cannot be accomplished by filtration. The compound can be sterilized by exposure to ethylene oxide before suspending in the sterile vehicle. Advantageously, a surfactant or wetting agent is included in the composition to facilitate uniform distribution of the compound.

Compositions for inhalation are of three basic types: (1) a powder mixture preferably micro-pulverized; (2) an aqueous solution to be sprayed with a nebulizer; and (3) an aerosol with volatile propellant in a pressurized container.

The powders are quite simply prepared by mixing a compound of the formula with a solid base which is compatible with lung tissue, preferably lactose. The powders are packaged in a device adapted to emit a measure amount of powder when inhaled through the mouth.

Aqueous solutions are prepared by dissolving the compound of the formula I in water and adding salt to provide an isotonic solution and buffering to a pH compatible with inhalation. The solutions are dispersed in a spray device or nebulizer and sprayed into the mouth inhaling.

Aerosols are prepared by dissolving a compound of the formula I in water or ethanol and mixing with a volatile propellant and placing in a pressurized container having a metering valve to release a predetermined amount of material.

The term "unit dosage form", as used in the specification and claims, refers to physically discrete units suitable as unitary dosages for human subjects and animals, each unit containing a predetermined quantity of active material calculated to produce the desired therapeutic effect in association with the required pharmaceutical diluent. carrier or vehicle. The specifications for the novel unit dosage forms of this invention are dictated by and directly dependent on (a) the unique characteristics of the active material and the particular effect to be achieved and (b) the limitations inherent in the art of compounding such an active material for use in humans and animals, as disclosed in detail in this specification, these being features of the present invention. Examples of suitable unit dosage forms in accord with this invention are tablets, capsules, pills, suppositories, powder packets, granules, wafers, cachets, teaspoonfuls, tablespoonfuls, dropperfuls, ampuls, vials, aerosols with metered discharges, segregated multiples of any of the foregoing, and other forms as herein described.

The dosage of the compound for treatment depends on the route of administration. A dosage schedule of from about 1.0 to 1000 mg. in a single dose administered orally, parenterally or by inhalation, embraces the effective range for preventing allergic attack for which the compositions are effective. The dosage to be administered is repeated up to 4 times daily.

The administration of the compositions of the present invention to humans and animals provides a method for the prophylactic treatment of allergy or all anaphylactic reactions of a reagin or non-reagin mediated nature. That is to say, these compositions when administered to a sensitized individual prior to the time that the individual comes into contact with substances (antigens), to which he is allergic, will prevent the allergic reaction which would otherwise occur.

For example, the process can be used for prophylactic treatment of such chronic conditions as bronchial asthma, allergic rhinitis, food allergy, hay fever, urticaria, and auto-immune diseases.

EXAMPLE 1

A lot of 10,000 tablets, each containing 25 mg. of 2-(6-methoxy-2-naphthyl)propionic acid is prepared from the following types and amounts of ingredients.

| | |
|---|---|
| 2-(6-methoxy-2-naphthyl)propionic acid | 250 gm. |
| Dicalcium phosphate | 1,500 gm. |
| Methcellulose, U.S.P. (15 cps.) | 60 gm. |
| Talc | 150 gm. |
| Corn Starch | 200 gm. |
| Calcium stearate | 12 gm. |

The compound and dicalcium phosphate are mixed well, granulated with 7.5 percent solution of methylcellulose in water, passed through a No. 8 screen and dried carefully. The dried granules are passed through a No 12 screen, mixed thoroughly with the talc, starch and magnesium stearate, and compressed into tablets.

These tablets are useful in preventing hay fever attacks at a dose of 1 tablet every four hours.

EXAMPLE 2

One thousand two-piece hard gelatin capsules, each containing 50 mg. of 2-(6-methoxy-2-naphthyl)propionic acid are prepared from the following types and amounts of ingredients:

| | |
|---|---|
| 2-(6-methoxy-2-naphthyl)propionic acid | 50 gm. |
| Talc | 100 gm. |
| Magnesium stearate | 10 gm. |

The ingredients are mixed well and filled into capsules of the proper size.

Capsules so prepared are useful in preventing attacks of bronchial asthma at a dose of one capsule every six hours.

EXAMPLE 3

One thousand tablets, each containing 100 mg. of 2-(6-methoxy-2-naphthyl)propionic acid are made from the following types and amounts of ingredients

| | |
|---|---|
| 2-(6-methoxy-2-naphthyl)propionic acid | 100 gm. |
| Microcrystalline cellulose NF | 120 gm. |
| Starch | 16 gm. |
| Magnesium stearate powder | 4 gm. |

The ingredients are screened and blended together and pressed into 100 mg. tablets.

The tablets are useful to protect against food allergy at a dose of 1 tablet before meals.

EXAMPLE 4

A sterile preparation suitable for inramuscular injection and containing 10 mg. of 2-(6-methoxy-2-naphthyl)propionic acid as the sodium salt in each milliliter is prepared from the following ingredients:

| | |
|---|---|
| 2-(6-methoxy-2-naphthyl)propionic acid sodium salt | 10.8 gm. |
| Benzyl benzoate | 200 ml. |
| Methylparaben | 1.5 gm. |
| Propylparaben | 0.5 gm. |
| Cottonseed oil q.s. | 1,000 ml. |

One milliliter of this sterile preparation is injected for prophylactic treatment of allergic rhinitis.

EXAMPLE 5

Aqueous Solution 600 ml. of an aqueous solution containing 500 mg. of 2-(6-methoxy-2-naphthyl)propionic acid is prepared as follows:

| | |
|---|---|
| 2-(6-methoxy-2-naphthyl)propionic acid sodium salt | 540 mg. |
| Sodium chloride | 5,400 mg. |
| Water for injection q.s. | 600 ml. |

The sodium chloride and 2-(6-methoxy-2-naphthyl)propionic acid sodium salt are dissolved in sufficient water to make 600 ml. and sterile filtered.

The solution is placed in nebulizers designed to deliver 0.25 ml. of solution per spray.

The solution is sprayed into the lungs every four hours for prevention of asthmatic attacks.

EXAMPLE 6

Powder for Insufflation

A powder mixture consisting of 500 mg. of 2-(6-methoxy-2-naphthyl)propionic acid and sufficient lactose to make 5 gm. of mixture is micropulverized and placed in an insufflator designed to deliver 50 mg. of powder per dose.

The powder is inhaled into the lungs for prevention of asthmatic attacks.

EXAMPLE 7

Aerosol

Twelve grams of an aerosol composition is prepared from the following ingredients:

| | |
|---|---|
| 2-(6-methoxy-2-naphthyl)propionic acid | 2.0 gm. |
| Absolute ethanol | 4.855 gm. |
| Freon 12 | 1.43 gm. |
| Freon 114 | 5.7 gm. |

The 2-(6-methoxy-2-naphthyl)propionic acid is dissolved in the ethanol and chilled to −30° C. and added to the chilled Freons. The 12 grams of composition is added to a 13 cc. plastic coated bottle and capped with a metering valve. The metering valve releases 80 mg. of composition in an aerosol.

The aerosol is inhaled every six hours for prevention of asthmatic attacks.

EXAMPLE 8

Following the procedure of the preceding Examples 1, 2, 3, 6, and 7, substituting an equimolar amount each of 2-(2'-naphthyl)propionic acid, 2-(6'-ethynyl-2'-naphthyl)propionic acid, 2-(6'-difluoromethylthio-2'-naphthyl)propionic acid, 2-(6'-difluoromethoxy-2'-naphthyl)propionic acid, 2-(7'-difluoromethoxy-2'-naphthyl)propionic acid, 2-(6'-hydroxy-2'-naphthyl)propionic acid, 2-(6'-methoxymethyloxy-2'-naphthyl)propionic acid, 2-(6'-methyl-2'-naphthyl)propionic acid, 2-(6'-methoxymethylthio-2'-naphthyl)propionic acid, 2-(7'-methoxymethylthio-2'-naphthyl)-3,3-difluoropropionic acid, 2-(6'-trifluoromethyl-2'-naphthyl)propionic acid, 2-(6'-ethyl-2'-naphthyl)propionic acid, 2-(6'-isopropyl-2'-naphthyl)propionic acid, 2-(6'-fluoro-2'-naphthyl)propionic acid, 2-(6'-chloro-2'-naphthyl)propionic acid, 2-(6'-acetyl-2'-naphthyl)propionic acid, 2-(6'-methylthio-2'-naphthyl)propionic acid, 2-(7'-chloro-2'-naphthyl)propionic acid, 2-(7'-methoxy-2'-naphthyl)propionic acid, 2-(7'-methyl-2'-naphthyl)propionic acid, 2-(8'-methyl-2'-naphthyl)propionic acid, 2-(8'-fluoro-2'-naphthyl)propionic acid, and 2-(6'-difluoromethoxy-2'-naphthyl)-3,3-difluoropropionic acid, for the compound of the Example, compositions are similarly prepared.

EXAMPLE 9

Following the procedure of the preceding Examples 4 and 5 substituting an equimolar amount each of the sodium, potassium or ammonium salts of the compounds of Example 8 for the compound of Examples 4 and 5, compositions are similarly prepared.

I claim:

1. A process for the prophylactic treatment of asthma comprising the systemic administration of from 1 to 1000 mg. of a compound of the formula:

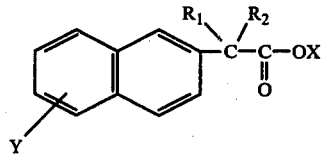

wherein Y is lower alkyl of 1 to 8 carbon atoms, cyclopropyl, ethinyl, $-CF_3$ $-F$, $-Cl$, $-OCH_3$ $-OCHF_2$, $-OCH_2OCH_3$, $-SCH_3$, $SCHF_2$, $-SCH_2OCH_3$, acetyl; $R_1$ and $R_2$ are H, $CH_3$, $CHF_2$, or taken together are $=CH_2$ or $=CF_2$1 and X is hydrogen, lower alkyl of 1 to 8 carbon atoms, or a pharmacologically acceptable cation in association with a pharmaceutical carrier to an asthmatic human or animal subject.

2. The process of claim 1 wherein the compound selected is 2-(6-methoxy-2-naphthyl)propionic acid.

3. The process of claim 1 wherein the allergy is asthma.

* * * * *